United States Patent
Caldwell et al.

(10) Patent No.: US 6,603,011 B1
(45) Date of Patent: *Aug. 5, 2003

(54) 3-PYRIDINYL COMPOUNDS

(75) Inventors: William Scott Caldwell, Winston-Salem, NC (US); Gary Maurice Dull, Lewisville, NC (US); Grayland Page Dobson, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/642,351

(22) Filed: Aug. 21, 2000

Related U.S. Application Data

(63) Continuation of application No. 08/631,761, filed on Apr. 23, 1996.

(51) Int. Cl.$^7$ .............................................. C07D 213/38
(52) U.S. Cl. ....................... 546/329; 546/286; 546/290; 546/294; 546/297; 546/298; 546/300
(58) Field of Search .................. 546/286, 290, 546/294, 297, 298, 300, 329

(56) References Cited

U.S. PATENT DOCUMENTS

| | | | |
|---|---|---|---|
| 4,684,654 A | 8/1987 | Wright et al. | 514/259 |
| 5,212,188 A | 5/1993 | Caldwell et al. | 514/343 |
| 5,283,363 A | 2/1994 | Kuhnt et al. | 564/336 |
| 5,356,906 A | 10/1994 | Ciganek et al. | 514/323 |
| 5,597,919 A | 1/1997 | Dull et al. | 544/242 |
| 5,616,707 A | 4/1997 | Crooks et al. | 544/242 |
| 5,616,716 A * | 4/1997 | Dull et al. | 546/300 |
| 5,723,477 A | 3/1998 | McDonald et al. | 514/340 |

FOREIGN PATENT DOCUMENTS

WO     WO 96/20600     7/1996

OTHER PUBLICATIONS

Guthrie, R.W., et al., *Chem. Abstract* 110:212619 (1989).
Guthrie, R.W., et al., *J. Med. Chem.* 32:1820–1935 (1989).
Tomcufcik et al., *Chem. Abstract* 108:37830 (1988).
Tilley et al., *Chem. Abstract* 106:12535 (1987).
Seeman et al., *Chem. Abstract* 103:142236 (1985).
Cooper et al., "Femtogram On–column Detection of Nicotine by Isotope Dilution Gas Chromatography/Negative Ion Detection Mass Spectrometry," Biological Mass Spectrometry, vol. 22 (1993).
Pinner, A., "Ueber Nicotin (Metanicotin)," Chem. Ber., pp. 1053–1061, (1894).
Pinner, A., "Ueber Nicotin," Chem. Ber., pp. 2861–2870 (1894).
LaForge, F.B., "The Preparation and Properties of Some New Derivatives of Pyridine," J. Am. Chem. Soc., vol. 50, pp. 2477–2483 (1928).

Acheson, et al., "Transformations involving the Pyrrolidine Ring of Nictone," J. Chem. Soc., Perking Trans. 1, vol. 2, pp. 579–585 (1980).

Loffler et al., Chem. Ber., vo. 42, pp. 3431–3438 (1909).

Joyce, et al., "The Formation of 1–Methyl–3–Nicotinoylpyrrolidine from Nicotine–1'–Oxide," Heterocycles, vol. 29, No. 7, pp. 1335–13342 (1989).

Frank, et al., "Palladium–Catalyzed Vinylic Substitution Reactions with Heterocyclic Bromides," J. Org. Chem., vol. 43, No. 15, pp. 2947–2949 (1978).

Malek, et al., "Palladium–Catalyzed Synthesis of Cinnamylamines," J. Org. Chem., vol. 47, pp. 5395–5397 (1982).

Sprouse, et al., "Isomers of metanicotine and the Pinner–Etard reaction," In Abstracts of Papers, Coresta/TCRC, pp. 32–33 (1972).

S. Arneric & M. Williams, "Nicotinic Agonists in Alzheimer's Disease: Does the Molecular Diversity of Nicotine Receptors Offer the Opportunity for Developing CNS–Selective Cholinergic Channel Activators?" *Int. Acad. Biomed. Drug Res.*, 7: 58–70 (1994).

Bencherif et al., "Metanicotine: A Nicotinic Agonist with CNS Selectivity—In Vitro Characterization," *Society for Neuroscience Abstracts*, 21(1–3): 605 (1995).

Perry et al., "Alteration in Nicotine Binding Sites in Parkinson's Disease, Lewy Body Dementia and Alzheimer's Disease: Possible Index of Early Neuropathology," *Elsevier Science Ltd.*, 64(2): 385–395 (1995).

B. Sahakian & J. Coull, "Nicotine and Tetrahydroaminoacradine: Evidence for Improved Attention in Patients with Dementia of the Alzheimer Type," *Drug Development Research*, 31: 80–88 (1994).

Wilson Jr. et al., "Nicotine–Like Actions of *cis*–Metanicotine and *trans*–Metanicotine," *The Journal of Pharmacology and Experimental Therapeutics*, 196(3): 685–696 (1976).

* cited by examiner

Primary Examiner—Deepak Rao
(74) Attorney, Agent, or Firm—Womble Carlyle Sandridge & Rice, PLLC

(57) ABSTRACT

Patients susceptible to or suffering from central nervous system disorders are treated by administering effective amounts of aryl substituted aliphatic amine compounds, aryl substituted olefinic amine compounds or aryl substituted acetylenic amine compounds. A representative compound is (E)-N-methyl-5-(3-pyridinyl)-4-penten-2-amine.

12 Claims, No Drawings

3-PYRIDINYL COMPOUNDS

This is a continuation application claiming the benefit of application Ser. No. 08/631,761 filed Apr. 23, 1996, the disclosure of which is incorporated herein by reference.

BACKGROUND OF THE INVENTION

The present invention relates to compounds having pharmaceutical properties, and in particular, to compounds useful for preventing and treating central nervous system (CNS) disorders. The present invention relates to a method for treating patients suffering from or susceptible to such disorders, and in particular, to a method for treating patients suffering from those disorders which are associated with neurotransmitter system dysfunction. The present invention also relates to compositions of matter useful as pharmaceutical compositions in the prevention and treatment of CNS disorders which have been attributed to neurotransmitter system dysfunction.

CNS disorders are a type of neurological disorder. CNS disorders can be drug induced; can be attributed to genetic predisposition, infection or trauma; or can be of unknown etiolog. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a doparminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

Senile dementia of the Alzheimer's type (SDAT) is a debilitating neurodegenerative disease, mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, Jones, et al., *Intern. J. Neurosci.*, Vol. 50, p. 147 (1990); Perry, *Br. Med. Bull.*, Vol. 42, p. 63 (1986) and Sitaram, et al., *Science*, Vol. 201, p. 274 (1978) It has been observed that nicotinic acetylcholine receptors, which bind nicotine and other nicotinic agonists with high affinity, are depleted during the progression of SDAT. See, Giacobini, *J. Neurosci. Res.*, Vol. 27, p. 548 (1990); and Baron, *Neurology*, Vol. 36, p. 1490 (1986). As such, it would seem desirable to provide therapeutic compounds which either directly activate nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. Biol.* Vol. 31, p. 191 (1987); and Marks, *J. Pharmacol. Exp. Ther.*, Vol. 226, p. 817 (1983). It also has been proposed that nicotine can act directly to elicit the release of acetylcholine in brain tissue, to improve cognitive functions, and to enhance attention. See, Rowell, et al., *J. Neurochem.*, Vol. 43, p. 1593 (1984); Sherwood, *Human Psychopharm.*, Vol. 8, pp. 155–184 (1993); Hodges, et al., *Bio. of Nic.*, Edit. by Lippiello, et al., p. 157 (1991); Sahakian, et al., *Br. J. Psych.*, Vol. 154, p. 797 (1989); and U.S. Pat. No. 4,965,074 to Leeson and U.S. Pat. No. 5,242,935 to Lippiello et al. Other methods for treating SDAT have been proposed, including U.S. Pat. No. 5,212,188 to Caldwell et al. and U.S. Pat. No. 5,227,391 to Caldwell et al. and European Patent Application No. 588,917. Another proposed treatment for SDAT is Cognex, which is a capsule containing tacrine hydrochloride, available from Parke-Davis Division of Warner-Lambert Company, which reportedly preserves existing acetylchloine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.*, Vol. 54, pp. 167–170 (1991) and Clark, et al., *Br. J. Pharm*, Vol. 85, pp. 827–835 (1985). It also has been proposed that nicotine can ameliorate the symptoms of PD. See, Smith et al., *Rev. Neurosci.*, Vol. 3(1), pp. 25–43 (1982).

Certain attempts have been made to treat PD. One proposed treatment for PD is Sinemet CR, which is a sustained-release tablet containing a mixture of carbidopa and levodopa, available from The DuPont Merck Pharmaceutical Co. Another proposed treatment for PD is Eldepryl, which is a tablet containing selefiline hydrochloride, available from Somerset Pharmaceuticals, Inc. Another proposed treatment for PD is Parlodel, which is a tablet containing bromocriptine ryiesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) varience in the clinical phenomenology of the tics, and (iv) occurrence of quasi daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. See, Calderon-Gonzalez et al., *Intern. Pediat.*, Vol. 8(2), pp. 176–188 (1993) and *Oxford Textbook of Medicine*, Eds. Weatherall et al., Chapter 21.218 (1987).

It has been proposed that nicotine pharmacology is beneficial in suppressing the symptoms associated with TS. See, Devor et al., *The Lancet*, Vol. 8670, p. 1046 (1989); Jarvik, *British J. of Addiction*, Vol. 86, pp. 571–575 (1991); McConville et al., *Am. J. Psychiatry*, Vol. 148 (6), pp. 793–794; (1991); Newhouse et al., *Brit. J. Addic.*, Vol. 86, pp.

521–526 (1991); McConville et al., *Biol, Psychiatry*, Vol. 31, pp. 832–840 (1992); and Sanberg et al., *Proceedings from Intl. Symp, Nic.*, S39 (1994). It also has been proposed to treat TS using Haldol, which is haloperidol available from McNeil Pharmaceutical; Catapres, which is clonidine available from Boehringer Ingelheim Pharmaceuticals, Inc.; Orap, which is pimozide available from Gate Pharmaceuticals; Prolixin, which is fluphenazine available from Apothecon Division of Bristol-Myers Squibb Co.; and Klonopin, which is clonazepam available from Hoffmann-LaRoche Inc.

Attention deficit disorder (ADD) is a disorder which affects mainly children, although ADD can affect adolescents and adults. See, Vinson, *Arch. Fam. Med.*, Vol. 3(5), pp. 445–451 (1994); Hechtman. *J. Psychiatry Neurosci.*, Vol. 19 (3), pp. 193–201 (1994); Faraone et al., *Biol. Psychiatry*, Vol. 35(6), pp. 398–402 (1994) and Malone et al., *J. Child Neurol.*, Vol. 9(2), pp. 181–189 (1994). Subjects suffering from the disorder typically have difficulty concentrating, listening, learning and completing tasks; and are restless, fidgety, impulsive and easily distracted. Attention deficit disorder with hyperactivity (ADHD) includes the symptoms of ADD as well as a high level of activity (e.g., restlessness and movement). Attempts to treat ADD have involved administration of Dexedrine, which is a sustained release capsule containing detroamphetamine sulfate, available from SmithKline Beecham Pharmaceuticals; Ritalin, which is a tablet containing methylphenidate hydrochloride, available from Ciba Pharmaceutical Company; and Cylert, which is a tablet containing premoline, available from Abbott Laboratories. In addition, it has been reported that administration of nicotine to an individual improves that individual's selective and sustained attention. See, Warburton et al., *Cholinergic control of cognitive resources, Neuropsychobiology*, Eds. Mendlewicz, et al., pp 43–46 (1993).

Schizophrenia is characterized by psychotic symptoms including delusions, catatonic behavior and prominent hallucinations, and ultimately results in a profound decline in the psychosocial affect of the subject suffering therefrom. Traditionally, schizophrenia has been treated with Klonopin, which is available as a tablet containing clonezepam, available from Hoffmann-LaRoche Inc.; Thorazine, which is available as a tablet containing chlorpromazine, available from SmithKline Beecham Pharrmaceuticals; and Clozaril which is a tablet containing clozapine, available from Sandoz Pharmaceuticals. Such neuroleptics are believed to be effective as a result of interaction thereof with the dopaminergic pathways of the CNS. In addition, a dopaminergic dysfunction possessed by individuals suffering from schizophrenia has been proposed. See, Lieberman et al., *Schizophr. Bull.*, Vol. 19, pp. 371–429 (1993) and Glassman, *Amer. J. Psychiatry*, Vol. 150, pp. 546–553 (1993). Nicotine has been proposed as being effective in effecting neurotransmitter disfunction associated with schizophrenia. See, Merriam et al., *Psychiatr. Annals*, Vol. 23, pp. 171–178 (1993) and Adler et al., *Biol. Psychiatry*, Vol. 32, pp. 607–616 (1992).

Nicotine has been proposed to have a number of pharmacological effects. Certain of those effects may be related to effects upon neurotransmitter release. See, for example, Sjak-shie et al., *Brain Res.*, Vol. 624, pp. 295–298 (1993), where neuroprotective effects of nicotine are proposed. Release of acetylcholine and dopamine by neurons upon administration of nicotine has been reported by Rowell et al., *J. Neurochem.*, Vol. 43, pp. 1593–1598 (1984); Rapier et al., *J. Neurochem.*, Vol. 50, pp. 1123–1130 (1988); Sandor et al., *Brain Res.*, Vol. 567, pp. 313–316 (1991) and Vizi, *Br. J. Pharmacol.*, Vol. 47, pp. 765–777 (1973). Release of norepinephrine by neurons upon administration of nicotine has been reported by Hall et al., *Biochem. Pharmacol.*, Vol. 21, pp. 1829–1838 (1972). Release of serotonin by neurons upon administration of nicotine has been reported by Hery et al., *Arch. Int. Pharmacodyn. Ther.*, Vol.296, pp. 91–97 (1977). Release of glutamate by neurons upon administration of nicotine has been reported by Toth et al., *Neurochem Res.*, Vol. 17, pp. 265–271 (1992). Therefore, it would be desirable to provide a pharmaceutical composition containing an active ingredient having nicotinic pharmacology, which pharmaceutical composition is capable of illiciting neurotransmitter release within a subject in order to prevent or treat a neurological disorder. In addition, nicotine reportedly potentiates the pharmacological behavior of certain pharmaceutical compositions used for the treatment of certain CNS disorders. See, Sanberg et al., *Pharmacol. Biochem. & Behavior*, Vol. 46, pp. 303–307 (1993); Harsing et al. *J. Neurochem.*, Vol. 59, pp. 48–54 (1993) and Hughes, *Proceedings from Intl. Symp. Nic.*, S40 (1994). Furthermore, various other beneficial pharmacological effects of nicotine have been proposed. See, Decina et al., *Biol. Psychiatry*, Vol. 28, pp. 502–508 (1990); Wagner et al., *Pharmacopsychiatry*, Vol. 21, pp. 301–303 (1988); Pomerleau et al., *Addictive Behaviors*, Vol. 9, p. 265.(1984); Onaivi et al., *Life Sci.*, Vol. 54(3), pp. 193–202 (1994) and Hamon, *Trends in Pharmacol. Res.*, Vol. 15, pp. 36–39.

It would be desirable to provide a useful method for the prevention and treatment of a CNS disorder by administering a nicotinic compound to a patient susceptible to or suffering from such a disorder. It would be highly beneficial to provide individuals suffering from certain CNS disorders with interruption of the symptoms of those diseases by the administration of a pharmaceutical composition which has nicotinic pharmacology and which has a beneficial effect upon the functioning of the CNS, but which does not provide any significant associated side effects (e.g., increased heart rate and blood pressure) attendant with interaction of that compound with cardiovascular sites. It would be highly desirable to provide a pharmaceutical composition incorporating a compound which interacts with nicotinic receptors which have the potential to affect the functioning of the CNS, but which does not significantly affect those receptors which have the potential to induce undesirable side effects (e.g., appreciable pressor cardiovascular effects and appreciable activity at skeletal muscle sites).

SUMMARY OF THE INVENTION

The present invention relates to aryl substituted aliphatic amine compounds, aryl substituted olefinic amine compounds and aryl substituted acetylenic amine compounds. A representative compound is (E)-N-methyl-5 (3-pyridinyl)-4-penten-2-amine.

The present invention relates to a method for providing prevention or treatment of a central nervous system (CNS) disorder. The method involves administering to a subject an effective amount of a compound of the present invention.

The present invention, in another aspect, relates to a pharmaceutical composition comprising an effective amount of a compound of the present invention. Such a pharmaceutical composition incorporates a compound which has the capability of interacting with relevant nicotinic receptor sites of a subject, and hence has the capability of acting as a therapeutic in the prevention or treatment of a CNS disorder.

The pharmaceutical compositions of the present invention are useful for the prevention and treatment of CNS disorders. The pharmaceutical compositions provide therapeutic benefit to individuals suffering from certain CNS disorders and exhibiting clinical manifestations of such disorders in that the compounds within those compositions have the potential to (i) exhibit nicotinic pharmacology and affect nicotinic receptors sites in the CNS (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) not provide appreciable adverse side effects (e.g., significant increases in blood pressure and heart rate, and significant effects upon skeletal muscle). The pharmaceutical compositions of the present invention are believed to be safe and effective with regards to prevention and treatment of CNS disorders.

DETAILED DESCRIPTION OF THE PREFERRED EMBODIMENTS

The present invention, in one aspect, relates to certain compounds having the formula:

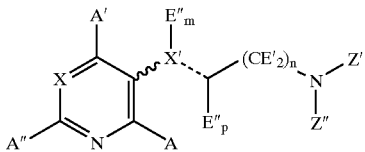

where X is nitrogen or carbon bonded to a substituent species characterized as having a sigma m value greater than 0, often greater than 0.1, generally greater than 0.2 and even greater than 0.3; less than 0 and generally less than −0.1; or 0; as determined in accordance with Hansch et al., Chem, Rev., Vol.91, pp. 165–195(1991); n is an integer which is 1, 2, 3, 4, 5, 6 or 7, preferably is 1, 2 or 3, and most preferably is 2 or 3; E' represents hydrogen or lower alkyl ( e.g., straight chain or branched alkyl including $C_1$–$C_5$, such as methyl, ethyl or isopropyl) or halo substituted lower alkyl (e.g., straight chain or branched alkyl including $C_1$–$C_5$, such as trifluormethyl or trichloromethyl); E" represents lower alkyl (e.g., straight chain or branched alkyl including $C_1$–$C_5$, such as methyl, ethyl or isopropyl) or halo substituted lower alkyl (e.g., straight chain or branched alkyl including $C_1$–$C_5$, such as trifluormethyl or trichloromethyl); Z' and Z" individually represent hydrogen or lower alkyl (e.g., straight chain or branched alkyl including $C_1$–$C_5$, such as methyl, ethyl or isopropyl), and preferably at least one of Z' and Z" is hydrogen, and most preferably Z' is hydrogen and Z" is methyl; alternatively Z' is hydrogen and Z" represents a ring structure, such as cyclopropyl, cyclobutyl, cyclopentyl, cyclohexyl, cycloheptyl, adamantyl, quinuclidinyl, pyridinyl, quinolinyl, pyrinidinyl, phenyl, alkyl or halo substituted phenyl, benzyl, or alkyl or halo substituted benzyl; alternatively Z', Z" and the associated nitrogen atom can form a ring structure, such as aziridinyl, azetidinyl, pyrollidinyl, piperidinyl, piperazinyl or morpholinyl; A, A' and A" individually represent hydrogen, alkyl (e.g., lower straight chain or branched alkyl, including $C_1$–$C_7$, but preferably methyl or ethyl) or halo (e.g., F. Cl, Br or I); the dashed line in the structure represents a C—C single bond, a C—C double bond or a C—C triple bond; m is 0 or 1 when the dashed line is a C—C single or C—C double bond, and 0 when the dashed line is a C—C triple bond; p is 0 or 1 when the dashed line is a C—C single or C—C double bond, and 0 when the dashed line is a C—C triple bond; the wavy line in the structure represents a cis (Z) or trans (E) form of the compound when the dashed line is a C—C double bond; and X' represents $CH_2$ (m=0) or CHE" (m=1) when the dashed line is a C—C single bond, CH or CE" when the dashed line is a C—C double bond, and C when the dashed line is a C—C triple bond. X includes N, C—H, C—F, C—Cl , C—Br, C—I, C—NR'R", C—$CF_3$, C—OH, C—CN, C—$C_2$R', C—SH, C—$SCH_3$, C—$N_3$, C—$SO_2CH_3$, C—OR', C—SR', C—C(=O)NR'R", C—NR'C(=O)R', C—(C=O)R', C—C(=O)OR', —$CCH_2$OR', C—OC(=O) R', COC(=O)NR'R" and C—NR'C(=O)OR' where R' and R" are individually hydrogen, lower alkyl (e.g., alkyl containing one to five carbon atoms, preferably methyl, ethyl or isopropyl), an aromatic group-containing species or a substituted aromatic group-containing species. When X represents a carbon atom bonded to a substituent species, that substitutent species often has a sigma m value which is between about −0.3 and about 0.75, and frequently between about −0.25 and about 0.6. In certain circumstances when X represents a carbon atom bonded to a substituent species, the dashed line is a C—C double bond and the compound has the trans (E) form, the substituent species is characterized as having a sigma m value not equal to 0. Particularly when the dashed line is a C—C double bond, the compound has the trans (E) form, A, A', A" and Z" all are hydrogen, n is 2, and Z" is hydrogen or methyl, the substituent species is characterized as having a sigma m value not equal to 0. Particularly when the dashed line is a C—C double bond, the compound has the trans (E) form, A, A', A" and Z' all are hydrogen, n is 2, and Z" is hydrogen or methyl, at least one of E' or E" is lower alkyl or halo substituted lower alkyl. In addition, it is highly preferred that A is hydrogen, it is preferred that A' is hydrogen, and normally A" is hydrogen. Generally, both A and A' are hydrogen; sometimes A and A' are hydrogen, and A" is methyl or ethyl; and often A, A' and A" are all hydrogen. Depending upon the identity and positioning of each individual E' or E", certain compounds can be optically active. Typically, the values of each of m and p, and the selection of E', are such that up to about 4, and frequently up to 3, of the substituents designated as E' and E" are non-hydrogen substituents (i.e., substituents such as lower alkyl or halo-substituted lower alkyl).

Representative compounds are N-methyl-4-(3-pyridinyl)-2-methylbutan-1-amine, N-methyl-4-(3-pyridinyl)-3-methylbutan-1-amine, N-methyl-5-(3-pyridinyl)-pentan-1-amine, N-methyl-6-(3-pyridinyl)-hexan-3-amine, N-methyl-5-(3-pyridinyl)-2-methylpentan-2-amine, N-methyl-5-(3-pyridinyl)-3-methylpentan-2-amine, N-methyl-5-(3-pyridinyl)-pentan-2-amine, N-methyl-5-(3-pyridinyl)- 1,1,1-trifluoropentan-2-amine, N-methyl-5-(3-pyridinyl)-4-methylpentan-1-amine, N-methyl-5-(3-pyridinyl)-4-methylpentan-2-amine, N-methyl-1-(3-pyridinyl)-octan-4-amine, N-methyl-1-(3-pyridinyl)-5-methylheptan-4-amine, N-methyl-6-(3-pydriinyl)-2,4-dimethylhexan-2-amine, N-methyl-6-(3-pyridinyl)-5-methylhexan-2-amine, N-methyl-6-(3-pyridinyl)-hexan-2-amine, N-methyl-6-(3-pyridinyl)-5-methylhexan-3-amine, 4-(3-pyridinyl)-2-methylbutan-1-amine,4-(3-pyridinyl)-3-methylbutan-1-amine, 5-(3-pyridinyl)-pentan-1-amine, 6-(3-pyridinyl)-hexan-3-amine, 5-(3-pyridinyl)-2-methylpentan-2-amine, 5-(3-pyridinyl)-3-methylpentan-2-amine, 5-(3-pyridinyl)-pentan-2-amine, 5-(3-pyridinyl)-1,1,1-trifluoropentan-2-amine, 5-(3-pyridinyl)-4-methylpentan-1-amine, 5-(3-pyridinyl)-4-methylpentan-2-amine, 1-(3-pyridinyl)-octan-4-amine, 1-(3-pyridinyl)-3-methylheptan-5-amine, 6-(3-pyridinyl)-2,4-dimethylhexan-2-amine, 6-(3-pyridinyl)-5- methylhexan-2-amine, 6-(3-pyridinyl)-hexan-2-amine and 6-(3-pyridinyl)-5-methylhexan-3-amine.

Other representative compounds are N-methyl-5-(3-pyridinyl)-4-pentyn-2-amine, N-methyl-6-(3-pyridinyl)-5-hexyn-3-amine, N-methyl-1-(3-pyridinyl)-1-heptyn-4-amine, N-methyl-1-(3-pyridinyl)-1-octyn-4-amine, N-methyl-1-(3-pyridinyl)-1-nonyn-4-amine, N-methyl-5-(3-pyridinyl)-3-methyl-4-pentyn-2-amine, 5-(3-pyridinyl)-4-pentyn-2-amine, 6-(3-pyridinyl)-5-hexyn-3-amine, 1-(3-pyridinyl)-1-heptyn-4-amine, 1-(3-pyridinyl)-1-octyn-4-amine, 1-(3-pyridinyl)-1-nonyn-4-amine and 5-(3-pyridinyl)-3-methyl-4-pentyn-2-amine.

Of particular interest are compounds having the formula:

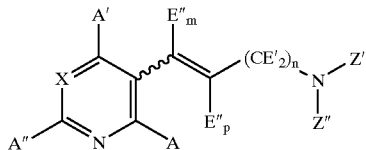

where n, m, p, X, A, A', A", E', E", Z' and Z" are as defined hereinbefore, and those compounds can have the cis (Z) or trans (E) form. For such compounds of pariticular interest, X most preferably is nitrogen or carbon bonded to a substituent species characterized as having a sigma m value greater than 0, often greater than 0.1, generally greater than 0.2 and even greater than 0.3; less than 0 and generally less than −0.1; or 0. One representative compound is (E)-N-methyl-4-[3-(5-ethoxypyridin)yl]-3-buten-1-amine for which X is C—OCH$_2$CH$_3$, n is 2, m is 0, p is 0, A, A', A" and Z' each are hydrogen, all E' are hydrogen and Z" is methyl. Another representative compound is (E)-4-[3-(5-methoxypyridin)yl]-3-buten-1-amine for which X is C—OCH$_3$, n is 2, m is 0, p is 0, all E' are hydrogen, and A, A', A", Z' and Z" each are hydrogen. Another representative compound is (E)-N-methyl-4-[3-(5-methoxypyridin)yl]-3-buten-1-amine for which X is C—OCH$_3$, n is 2, m is 0, p is 0, all E' are hydrogen, and A, A', A", and Z' are each hydrogen, and Z" is methyl. Another representative compound is (E)-4-[3-(5-ethoxypyridin)yl]-3-buten-1-amine for which X is C—OCH$_2$CH$_3$, n is 2, m is 0, p is 0, all E' are hydrogen, and A, A', A", Z' and Z" each are hydrogen. Another representative compound is (E)-4-[3-(5-methoxy-6-methylpyridin)yl]-3-buten-1-amine for which X is C—OCH$_3$, n is 2, m is 0, p is 0, all E' are hydrogen, A" is methyl, and A, A', Z' and Z" each are hydrogen. Another representative compound is (E)-N-methyl-4-[3-(5-methoxy-6-methylpyridin)yl]-3-buten-1-amine for which X is C—OCH$_3$, n is 2, m is 0, p is 0, all E' are hydrogen, A" and Z" each are methyl, and A, A' and Z' each are hydrogen. Another representative compound is (E)-N-methyl-4-[3-(5-hydroxymethylpyridin)yl]-3-buten-1-amine for which X is —CCH$_2$OH, n is 2, m is 0, p is 0, all E' are hydrogen, Z' is methyl and A, A', A" and Z" each are hydrogen.

Other representative compounds are (E) and (Z)-N-methyl-4-(3-pyridinyl)-2-methyl-3-buten-1-amine, (E) and (Z)-N-methyl-4-(3-pyridinyl)-3-methyl-3-buten-1-amine, (E) and (Z)-N-methyl-6-(3-pyridinyl)-5-hexen-3-amine, (E) and (Z)-N-methyl-5-(3-pyridinyl)-2-methyl-4-penten-2-amine, (E) and (Z)-N-methyl-5-(3-pyridinyl)-3-methyl-4-penten-2-amine, (E) and (Z)-N-methyl-5-(3-pyridinyl)-4-penten-2-amine, (E) and (Z)-N-methyl-5-(3-pyridinyl)-1,1,1-trifluoro-4-penten-2-amine, (E) and (Z)-N-methyl-5-(3-pyridinyl)-4-methyl-4-penten-1-amine, (E) and (Z)-N-methyl-5-(3-pyridinyl)-4-methyl-4-penten-2-amine, (E) and (Z)-N-methyl-1-(3-pyridinyl)-1-octen-4-amine, (E) and (Z)-N-methyl-1-(3-pyridinyl)-5-methyl-1-hepten-4-amine, (E) and (Z)-N-methyl-6-(3-pyridinyl)-2,4-dimethyl-5-hexen-2-amine, (E) and (Z)-N-methyl-6-(3-pyridinyl)-5-methyl-5-hexen-2-amine, (E) and (Z)-N-methyl-6-(3-pyridinyl)-5-hexen-2-amine, (E) and (Z)-N-methyl-6-(3-pyridinyl)-5-methyl-5-hexen-3-amine, (E) and (Z)-4-(3-pyridinyl)-2-methyl-3-buten-1-amine, (E) and (Z)-4-(3-pyridinyl)-3-methyl-3-buten-1-amine, (E) and (Z)-6-(3-pyridinyl)-5-hexen-3-amine, (E) and (Z)-5-(3-pyridinyl)-2-methyl-4-penten-2-amine, (E) and (Z)-5-(3-pyridinyl)-3-methyl-4-penten-2-amine, (E) and (Z)-5-(3-pyridinyl)-4-penten-2-amine, (E) and (Z)-5-(3-pyridinyl)-1,1,1-trifluoro-4-penten-2-amine, (E) and (Z)-5-(3-pyridinyl)-4-methyl-4-penten-1-amine, (E) and (Z)-5-(3-pyridinyl)-4-methyl-4-penten-2-amine, (E) and (Z)-1-(3-pyridinyl)-1-octen-4-amine, (E) and (Z)-1-(3-pyridinyl)-3-methyl-5-hepten-1-amine, (E) and (Z)-6-(3-pyridinyl)-2,4-dimethyl-5-hexen-2-amine, (E) and (Z)-6-(3-pyridinyl)-5-methyl-5-hexen-2-amine, (E) and (Z)-6-(3-pyridinyl)-5-hexen-2-amine, and (E) and (Z)-6-(3-pyridinyl)-5-methyl-5-hexen-3-amine. For such representative compounds at least one of m or p are 1 and/or at least one of E' is a non-hydrogen substituent.

The manner in which aryl substituted aliphatic amine compounds of the present invention are synthetically produced can vary. Preparation of various aryl substituted aliphatic amine compounds can be carried out using the types of techniques disclosed by Rondahl, *Acta Pharm. Suec.*, Vol. 13, pp. 229–234 (1976). Certain metanicotine-type compounds that possess a saturated side chain rather than an olefinic side chain can be prepared by hydrogenation of the corresponding metanicotine-type compounds or the corresponding acetylenic precursors. For example, a dihydrometanicotine-type compound can be prepared by hydrogenation of an (E)-metanicotine-type compound using the types of procedures described by Kamimura et al., *Agr. Biol. Chem.*, Vol. 27, No. 10, pp. 684–688 (1963).

The manner in which aryl substituted acetylenic amine compounds of the present invention are synthetically produced can vary. For example, an aryl substituted acetylenic amine compound, such as an N-methyl-4-(3-pyridinyl)-3-butyn-1-amine type compound, can be prepared using a series of synthetic steps: (i) conversion of 3-pyridinecarboxaldehyde to a 1,1-dihalo-2-(3-pyridinyl)-ethylene using a carbon tetrahalide and triphenylphosphine, (ii) side chain elaboration of this intermediate by reaction with butyl lithium and ethylene oxide, affording 4-(3-pyridinyl)-3-butyn-1-ol, (iii) conversion of this intermediate to its methanesulfonate ester, and (iv) mesylate displacement with methyl amine, affording an N-methyl-4-(3-pyridinyl)-3-butyn-1-amine type compound. Representative synthetic techniques for aryl substituted acetylenic compounds are set forth in U.S. Pat. No. 5,597,919, the disclosure of which is incorporated herein by reference. Representative alkylene oxides which can be employed include propylene oxide, 1,2-epoxybutane, 1,2-epoxypentane, 1,2-epoxyhexane, 1,2-epoxyheptane, (E)-2,3-epoxybutane and (Z)-2,3-epoxybutane. 5-Substituted-3-pyridinecarboxaldehydes, such as 5-ethoxy-3-pyridinecarboxaldehyde, also can be employed.

The manner in which aryl substituted olefinic amine compounds of the present invention are synthetically produced can vary. (E)-metanicotine-type compounds can be prepared using the techniques set forth by Löffler et al., *Chem. Ber.*, Vol. 42, pp. 3431–3438 (1909) and Laforge, *J.A.C.S.*, Vol. 50, p. 2477 (1928)from substituted nicotine-type compounds. Certain 6-substituted metanicotine-type compounds can be prepared from the corresponding 6-substituted nicotine-type compounds using the general methods of Acheson et al., *J. Chem. Soc., Perkin Trans.* 1, Vol. 2, pp. 579–585 (1980). The requisite precursors for such compounds, 6-substituted nicotine-type compounds, can be synthesized from 6-substituted nicotinic acid esters using the general methods disclosed by Rondahl, *Acta Pharm. Suec.*, Vol. 14, pp 113–118 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1, Vol. 2, pp.579–585 (1980). The 5-halo-substituted nicotine-type compounds (e.g., fluoro- and bromo-substituted nicotine-type compounds) and the 5-amino nicotine-type compounds can be prepared using the general procedures disclosed by Rondahl, *Act. Pharm. Suec.*, Vol. 14, pp. 113–118 (1977). The 5-trifluoromethyl nicotine-type compounds can be prepared using the techniques and materials set forth in Ashimori et al., *Chem. Pharm. Bull.*, Vol. 38(9), pp. 2446–2458 (1990) and Rondahl, *Acta. Pharm. Suec.*, Vol. 14, pp. 113–118 (1977).

Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo-substituted, 5-substituted pyridine compound or a 5-halo-substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., *J. Org. Chem.*, Vol. 43(15), pp. 2947–2949 (1978) and Malek et al., *J. Org. Chem.*, Vol. 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group then affords the desired metanicotine-type compound.

There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, metanicotine-type compounds can be prepared by the controlled hydrogenation of the corresponding acetylenic compound,(e.g., an N-methyl-4-(3-pyridinyl)-3-butyn-1-amine type compound). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively. Representative synthetic techniques for (Z)-metanicotine-type compounds are set forth in U.S. Pat. No. 5,597,919.

There are yet other methods by which aryl substituted olefinic amine compounds of the present invention can be synthetically produced. An olefinic alcohol, such as 5-hexen-2-ol, is condensed with an aromatic halide, such as 3-bromopyridine or 3-iodopyridine. Typically, the types of procedures set forth in Frank et al., *J. Org. Chem.* Vol. 43, pp. 2947–2949 (1978) and Malek et al., *J. Org. Chem.*, Vol. 47, pp. 5395–5397 (1982) involving a palladium-catalyzed coupling of an olefin and an aromatic halide are used. The olefinic alcohol optionally can be protected as a t-butyldimethylsilyl ether prior to the coupling. Desilylation then produces the olefinic alcohol. The alcohol condensation product then is converted to an amine using the type of procedures set forth in deCosta et al.,*J. Org. Chem.*, Vol. 35, pp. 4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-2-ol, 4-penten-1-ol, 5-hexen-3-ol, 3-methyl-3-buten-1-ol, 2-methyl-3-buten-1-ol, 2-methyl-4-penten-2-ol, 4-methyl-4-penten-1-ol, 4-methyl-4-penten-2-ol, 1-octen-4-ol 5-methyl-1-hepten-4-ol, 4-methyl-5-hexen-2-ol, 5-methyl-5-hexen-2-ol, 5-hexen-2-ol and 5-methyl-5-hexen-3-ol. Trifluormethyl-substituted olefinic alcohols, such as 1,1,1-trifluoro-4-penten-2-ol, can be prepared from 1-ethoky-2,2,2-trifluoro-ethanol and allyltrimethylsilane using the procedures of Kubota et al., *Tetrahedron Letters*, Vol. 33(10), pp. 1351–1354 (1992), or from trifluoroacetic acid ethyl ester and allyltributylstannane using the procedures of Ishihara et al., *Tetrahedron Letters*, Vol. 34(56), pp. 5777–5780 (1993). Certain olefinic alcoholsare optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefulic amine compound. Alternatively, substituents such as —OH, —$NH_2$ and —SH can be protected as corresponding acyl compounds, or substituents such as —$NH_2$ can be protected as a phthalimide functionality.

The compounds of the present invention can be employed in a free base form or in a salt form (e.g., as pharmaceutically acceptable salts, such as chloride, perchlorate, ascorbate, sulfate, tartrate, fumarate, citrate, malate, lactate or aspartate salts). One method for providing the compound in salt form is set forth in of U.S. Pat. No. 5,597,919. Another method for providing the compound in a fumaric salt form involves (i) dissolving one equivalent of the compound in ethanol, (ii) mixing the solution with two equivalents of fumaric acid, (iii) concentrating the resulting solution to dryness, (iv) dissolving the resulting solid in ethanol, and then (v) precipitating the monofumarate salt from the ethanol. Another method for providing the compound in a fumaric salt form involves (i) adding a solution of suitably pure compound dissolved in tetrahydrofuran to a refluxing solution of fumaric acid in a tetrahydrofuran/ethanol co-solvent mixture to form a precipitate, (ii) applying heat and additional ethanol to the mixture to dissolve the precipitate, (iii) cooling the resulting solution, and seeding the solution if necessary, to cause precipitation of salt, and (iv) filtering and collecting the salt.

The present invention relates to a method for providing prevention of a CNS disorder to a subject susceptible to such a disorder, and for providing treatment to a subject suffering from a CNS disorder. In particular, the method comprises administering to a patient an amount of a compound effective for providing some degree of prevention of the progression of the CNS disorder (i.e., provide protective effects), amelioration of the symptoms of the CNS disorder, and amelioration of the reoccurrence of the CNS disorder. The method involves administering an effective amount of a compound selected from the general formulae which are set forth hereinbefore. The present invention relates to a pharmaceutical composition incorporating a compound selected from the general formulae which are set forth hereinbefore. Optically active compounds can be employed as racemic mixtures or as enantiomers. CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular CNS disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS.

The dose of the compound is that amount effective to prevent occurrence of the symptoms of the disorder or to treat some symptoms of the disorder from which the patient suffers. By "effective amount", "therapeutic amount" or "effective dose" is meant that amount.sufficient to elicit the desired pharmacological or therapeutic effects, thus resulting in effective prevention or treatment of the disorder. Thus, an effective amount of compound is an amount sufficient to pass across the blood-brain barrier of the subject, to bind to relevant receptor sites in the brain of the subject, and to elicit neuropharmacological effects (e.g., elicit neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount of at least about 1, often at least about 10, and frequently at least about 25 mg/24 hr./patient. For human patients, the effective dose of typical compounds requires administering the compound which generally does not exceed about 500, often does not exceed about 400, and frequently does not exceed about 300 mg/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds useful in carrying out the present invention generally are greater than 0, often are greater than about 0.5, and frequently are greater than about 1. The log P values of such typical compounds generally are less than about 3.0, and generally are less than about 2.5. Log P values provide a measure of the ability of a compound to pass across a diffusion barrier, such as a biological membrane. See, Hansch, et al., *J. Med. Chem.*, Vol. 11, p. 1 (1968).

The compounds useful according to the method of the present invention have the ability to bind to, and cause activation of, nicotinic cholinergic receptors of the brain of the patient. As such, such compounds have the ability to express nicotinic pharmacology, and in particular, to act as nicotinic agonists. The receptor binding constants of typical compounds useful in carrying out the present invention generally exceed about 1 nM, and often exceed about 5 nM. The receptor binding constants of such typical compounds generally are less than about 10 μM, often are less than about 1 uM, and frequently are less than about 100 nM. Receptor binding constants provide a measure of the ability of the compound to bind to half of the relevant receptor sites of certain brain cells of the patient. See, Cheng, et al., *Biochem. Pharmacol.*, Vol. 22, pp. 3099–3108 (1973).

The compounds useful according to the method of the present invention have the ability to demonstrate a nicotinic function by effectively eliciting ion flux through, and neurotransmitter secretion from, nerve ending preparations (i.e., thalamic or striatal synaptosomes). As such, such compounds have the ability to cause relevant neurons to become activated, and to release or secrete acetylcholine, dopamine, and other neurotransmitters. Generally, typical compounds useful in carrying out the present invention effectively provide for relevant receptor activation in amounts of at least about 30 percent, often at least about 50 percent, and frequently at least about 75 percent, of that maximally provided by (S)-(−)-nicotine. Generally, typical compounds useful in carrying out the present invention are more potent than (S)-(−)-nicotine in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine. Certain compounds of the present invention can provide secretion of dopamine in an amount which can exceed that maximally provided by (S)-(−)-nicotine. Generally, typical compounds useful in carrying out the present invention are less potent than (S)-(−)-nicotine in eliciting neurotransmitter secretion, such as dopamine secretion.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations derived from muscle preparations. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 1 mM). Generally, typical compounds useful in carrying the present invention activate isotopic rubidium ion flux by less than 5 percent of that maximally provided by (S)-(−)-nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical compounds useful in carrying the present invention activate isotopic rubidium ion flux by less than 10 percent, often by less than 5 percent, of that maximally provided by S(−) nicotine.

Compounds of the present invention, when employed in effective amounts in accordance with the method of the present invention, are effective towards providing some degree of prevention of the progression of CNS disorders, amelioration of the symptoms of CNS disorders, and amelioration to some degree of the reoccurrence of CNS disorders. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than 1/5, and often less than 1/10, that amount sufficient to cause any side effects to a significant degree.

The following example is provided in order to further illustrate various embodiments of the invention but should not be construed as limiting the scope thereof. Unless otherwise noted, all parts and percentages are by weight.

EXAMPLE

Sample No. 1 is 5-ethoxy-metanicotine or ( E)-N-methyl-4-[3-(5-ethoxypyridin)yl]-3-buten-1-amine, which was prepared essentially in accordance with the following techniques:

3-Bromo-5-ethoxypyrldine 3,5-Dibromopyridine (98%) was purchased from Lancaster Chemical Company. Sodium ethoxide (96%) and N,N-dimethylformamide DMF) (99.9+%, HPLC grade) were purchased from Aldrich Chemical Company. Under a nitrogen atmosphere, a mixture of 3,5-dibromopyridine (5.00 g, 21.1 mmol), sodium ethoxide (2.87 g, 42.2 mmol), and DMF (10 mL) was stirred and heated at 65° C. for 15 h. The mixture was poured into water (70 mL), and anhydrous diethyl ether (155 mL) was added. Because of insoluble solids, it was necessary to filter both phases. The aqueous layer was separated and extracted with ether (2×25, 3×50 mL). The combined ether extracts were dried ($MgSO_4$), filtered, and concentrated by rotary evaporation, producing a dark-brown syrup. The brown residue was purified by vacuum distillation, affording 0.76 g (17.9%) of an oil, bp 105° C. at 5 mm Hg. $^1$H NMR ($CDCl_3$): δ 9.12 (br s, 1H), 8.83 (br s, 1H), 8.42 (dd, 1H), 4.41 (q, 2H), 1.42 (t, 3H), $^{13}$C NMR ($CDCl_3$): δ 142.72, 136.50, 123.78, 64.31, 14.57.

(E)-4-[3-(5-Ethoxypyridin)yl]-3-buten-1-ol

3-Buten-1-ol (99%) was purchased from Aldrich Chemical Company. Under a nitrogen atmosphere, a mixture of 3-buten-1-ol (144 mg, 2.0 mmol), 3-bromo-5-ethoxypyridine (424 mg, 2.1 mmol), palladium(II) acetate (5 mg, 0.02 mmol), tri-o-tolylphosphine (25 mg, 0.08 mmol), triethylamine (0.5 mL), and acetonitrile (1.0 mL) was stirred and heated under reflux for 21 h. Upon cooling, the mixture was diluted with water (10 mL) and extracted with methylene chloride (2×5 mL). The combined methylene chloride extracts were dried ($Na_2SO_4$), filtered, and concentrated via rotary evaporation to give a dark-yellow gum (423 mg).

Purification by column chromatography on silica gel, eluting with methanol (2→8%) in ethyl acetate afforded 256 mg (66.3%) of an almost colorless oil. $^1$H NMR (CDCl$_3$): δ 8.15 (s, 1H), 8.12 (s, 1H), 7.14 (dd, 1H), 6.44 (d, 1H), 6.32–6.22 (dt, 1H), 4.06 (q, 2H), 3.77 (t, 2H), 2.49 (m, 2H), 1.42 (t, 3H). $^{13}$C NMR (CDCl$_3$): δ 155.08, 140.48, 136.69, 133.46, 129.22, 129.00, 117.43, 63.87, 61.85, 36.43, 14.73.

(E)-N-Methyl-4-[3-(5-ethoxypyridin)yl]-3-buten-1-amine

Under a nitrogen atmosphere, a cold (0° C.), stirring solution of (E)-4-[3-(5-ethoxypyridin)yl]-3-buten-1-ol (240 mg, 1.24 mmol), methylene chloride (1 mL), and pyridine (1 drop) was treated with tosyl chloride (260 mg, 1.36 mmol). The mixture was allowed to warm to room temperature. After stirring for 12 h, the solution was concentrated by rotary evaporation. The resulting residue was dissolved in methanol (3 mL) and 40% aqueous methylamine (3 mL) was added. The solution was stirred 5 h at room temperature and was then concentrated by rotary evaporation, affording the crude product (593 mg). The residue was partitioned between 1 M NaOH (2 mL) and chloroform (5 mL). The chloroform layer was separated, washed with water (2 mL), dried (Na$_2$SO$_4$), filtered, and concentrated via rotary evaporation to give a dark oil (276 mg). The oil was purified by column chromatography on silica gel, eluting with triethylamine-methanol (2.5:97.5). Selected fractions were combined and concentrated via rotary evaporation to give 87 mg (34.0%) of a light-brown oil, which quickly darkened. $^1$H, NMR (CDCl$_3$): δ 8.14 (d, 1H, J=1.8 Hz), 8.12 (d, 1H, J=2.7 Hz), 7.13 (dd, 1H, J=2.8, 1.7 Hz), 6.40 (d, 1H, J=16.0 Hz), 6.29–6.19 (dt, 1H, J=16.0, 6.8 Hz), 4.06, (q, 2H, J=7.0 Hz), 2.72 (t, 2H, J=6.8 Hz), 2.44 (s, 3H), 2.43 (dt, 2H, J=6.8 Hz), 1.76 (br s, 1H), 1.41 (t, 3H, J=7.0 Hz). $^{13}$C NMR (CDCl$_3$): δ 155.07, 140.48, 136.57, 133.59, 130.65, 128.09; 117.41, 63.85, 50.94, 36.14, 33.30, 14.72.

Sample No. 2 is (E)-N-methyl-5-(3-pyridinyl)-4-penten-2-amine, which is prepared essentially in accordance with the following techniques:

5-(3-Pyridinyl)-4-penten-2-ol

4-Penten-2-ol was purchased from Aldrich Chemical Company. Under a nitrogen atmosphere, a mixture of 3-bromopyridine (3.0 g, 19 mmol), 4-penten-2-ol (1.69 g, 19.6 mmol), palladium (II) acetate (42.6 mg, 0.19 mmol), tri-o-tolylphosphine (116 mg, 0.38 mmol), and triethylamine (3.85 g, 38 mmol) was stirred at 90° C. for 16 h. Triethylamine (1.45 g, 14 mmol) was added to the brown mixture which was allowed to stir an additional hour. The mixture was diluted with methylene chloride (20 mL) and water (20 mL). The aqueous phase was separated and extracted with methylene chloride (2×10 mL). The combined organic phases were washed with 25 mL water, dried with Na$_2$SO$_4$, filtered, and concentrated by rotary evaporation to give the compound as a dark yelow oil (3.05 g, 98%). Purification of the material was done by column chromatography on silica gel (225 g) eluting with EtOAc-MeOH (4:1). Combined fractions containing 5-(3-pyridinyl)-4-penten-2-ol, as determined by TLC analysis yielded 2.69 g (88.2%) of a yellow oil. TLC (EtOAc-MeOH, 4:1): R$_f$ 0.60. $^1$H NMR (CDCl$_3$, 300 MHz): δ 8.55 (d, 1H), 8.42 (dd, 1H), 7.67 and 7.64(dt, 1H), 7.23–7.18 (m, 1H), 6.44 (d, 1H), 6.33 and 6.27 (dt, 1H), 3.95 (m, 1H), 2.47–2.3 (m, 2H), 1.25 (d, 3H).

(E)-N-Methyl-5-(3-pyridinyl)-4-penten-2-amine

Under a nitrogen atmosphere, methanesulfonyl chloride (2.02 g, 17.7 mmol) was added dropwise to a stirring ice-cold solution of 5-(3-pyridinyl)-4-penten-2-ol (2.62 g, 16.1 mmol), triethylamine (3.25 g, 32.1 mmol) and tetrahydrofuran (THF) (5 mL). After one hour of stirring, additional THF (12 mL) and methanesulfonyl chloride (184 mg, 1.6 mmol) were added. The mixture was allowed to stir an additional 16 h. The dark-brown material was dissolved in water (50 mL), extracted with CHCl$_3$ (3×50 mL), dried (Na$_2$SO$_4$), filtered, and concentrated to give a mesylate (3.12 g, 80.6%) as a yellow oil. Methylamine (102 mL) was added to the mesylate (2.55 g, 10.6 mmol), and the mixture was allowed to stir at room temperature for ~17 h. The solution was basified with NaOH (one pellet) and extracted with diethyl ether (4×50 mL). The combined ether extracts were dried (Na$_2$SO$_4$), filtered, and concentrated to a yellow syrup. Water (50 mL) was added to the residue. The pH was adjusted to 8.27 with concentrated HCl, and the solution was extracted with CH$_2$Cl$_2$ (3×25 mL) to remove impurities. The aqueous layer was separated, the pH was adjusted to 13.0 using 50% NaOH solution and the resulting solution was extracted with methyl tert-butyl ether (MTBE) (5×25 mL). The combined MTBE layers were dried (Na$_2$SO$_4$), filtered, and concentrated by rotary evaporation to yield 668 mg of a yellow oil. The oil (500 mg) was further purified by vacuum distillation to give 184.8 mg of an oil, bp 80° C. at 0.05 mm Hg. Further purification by pH adjustment and extraction with MTBE and workup as described above afforded 127 mg (6.9%) of a yellow oil. $^1$H NMR (CDCl$_3$, 300 MHz): δ 8.55 (d, 1H, J=2.1 Hz, H-2), 8.41 (dd, 1H, J=1.6, 4.8 Hz, H-6), 7.66 and 7.63 (dt, 1H, J=2.0, 8.1 Hz, H-4), 7.20 (m, 1H, J=4.8, 1.5, 8.1 Hz, H-5), 6.40 (d, 1H, J=15.9 Hz, H-5'), 6.28 and 6.23 (dt, 1H, J=15.9, 7.0 Hz, H-4'), 2.68 (m, 1H, J=6.2 Hz, H-2'), 2.41 (s, 3H, N—CH$_3$), 2.39–2.22 (m, 2H, J=6.2,7.0 Hz, H-3'), 1.40 (br s, 1H, —NH) 1.08 (d, 3H, J=6.2 Hz, H-1'). $^{13}$C NMR (CDCl$_3$, 75 MHz): δ 148.2 (C-6), 148.0 (C-2), 133.0 (C-3), 132.5 (C-4), 130.0 (C-4'), 128.8 (C-5'), 123.3 (C-5), 54.6 (C-2'), 40.5 (C-3'), 34.0 (C-1'), 19.9 (N—CH$_3$).

EI-MS: 175 (M$^+$).

Sample No. 3 is 5-methoxy-metanicotine or (E)-N-methyl-4-[3-(5-methoxypyridin)yl]-3-buten-1-amine, which was prepared essentially in accordance with the following techniques:

3-Bromo-5-methoxypyridine

This compound was prepared using the general procedure of Comins et al, *J. Org. Chem.* Vol. 55, pp. 69–73 (1990).

4-[(Tert-Butyldimethylsilyl)oxy]-1-butene

Under a nitrogen atmosphere, to a cold (0° C.), stirring solution of 3-buten-1-ol (2.16 g, 30.0 mmol), pyridine (9 mL), and methylene chloride (30 mL) was added tert-butyldimethylsilyl chloride (4.53 g, 30.1 mmol) purchased from Aldrich Chemical Company. The ice-bath was removed and the mixture was allowed to stir 1 h at room temperature. The mixture, containing a white precipitate, was poured into water (60 mL) and shaken. The methylene chloride layer was separated from the aqueous layer, and the aqueous layer extracted with methylene chloride (30 mL). The two resulting organic extracts were combined, washed twice with water, dried (Na$_2$SO$_4$), filtered, and evaporated to give 8.94 g of crude product. Vacuum distillation afforded several fractions, the fraction with bp 80–82° C. at 35 mm Hg was collected to give 3.14 g (56.3%) of product as an oil. $^1$H NMR (CDCl$_3$): δ 5.86–5.73 (m, 1H), 5.08–4.98 (m, 2H), 3.64 (t, 2H), 2.29–2.22 (m, 2H), 0.87 (s, 9H), 0.03 (s, 6H).

(E)-4-[(Tert-Butyldimethylsilyl)oxy]-1-[3-(5-methoxypyridin)yl]-1-butene

Under a nitrogen atmosphere, a mixture 4-[(tert-butyldimethylsilyl)oxy]-1-butene (745 mg, 4.0 mmol), 3-bromo-5-methoxypyridine (790 mg of 90% purity, 4.2 mmol), palladium(II) acetate (10 mg, 0.045 mmol), tri-o-tolylphosphine (50 mg, 0.16 mmol), triethylanine (1.0 mL), and acetonitrile (2.0 mL) was stirred and heated under reflux for 20 h. Upon cooling, the mixture was diluted with water (20 mL) and extracted with methylene chloride (2×15 mL). The combined methylene chloride extracts were washed with water, dried ($Na_2SO_4$), filtered, a concentrated via rotary evaporation to give a brown oil (1.25 g, quantitative yield).

(E)-4-[3-(5-Methoxypyridin)yl]-3-buten-1-ol

A solution (E)-4-[(tert-butyldimethylsilyl)oxy]-1-[3-(5-methoxypyridin)yl]- 1-butene (1.25 g, 4.00 mmol) in ethanol (5 mL) was treated at room temperature with 1 M HCl (5 mL). The solution was stirred for 20 min and then concentrated via rotary evaporation. After further drying under high vacuum, the residue was treated with saturated, aqueous $NaHCO_3$ solution (5 mL) and partitioned between water (20 mL) and ether (30 mL). The aqueous layer was separated, saturated with NaCl, and extracted with ether (20 mL). The combined ether extracts were dried ($Na_2SO_4$), filtered, and then concentrated by rotary evaporation to give a viscous, yellow oil (632 mg). The product was purified by column chromatography on silica gel, eluting with methanol (3→12%) in ethyl acetate. Selected fractions were combined and concentrated via rotary evaporation to give 408 mg (56.9%) of an almost colorless oil. $^1$H NMR ($CDCl_3$): δ 8.14 (s, 1H), 8.16 (s, 1H), 7.15 (dd, 1H), 6.32 (d, 1H), 6.33–6.23 (dt, 1H), 3.84 (s, 3H), 3.77 (t, 2H), 2.53–2.46 (m, 2H).

(E)-N-Methyl-4-[3-(5-methoxypyridin)yl]-3-buten-1-amine

Under a nitrogen atmosphere, a solution of (E)-4-[3-(5-methoxypyridin)yl]-3-buten-1-ol (387 mg, 2.16 mmol), methylene chloride (1 mL), and pyridine (2 drops) was cooled to (0° C.). Tosyl chloride (433 mg, 2.27 mmol) was then added, and the solution was allowed to warm to room temperature. After stirring for 12 h, the solution was concentrated by rotary evaporation to a light-yellow gum (897 mg). The gummy residue was dissolved in methanol (4 mL) and 40% aqueous methylamine (4 mL) was added. The solution was stirred 6 h at room temperature and was then concentrated by rotary evaporation. Further drying under high vacuum afforded a brown gum (936 mg). The residue was partitioned between 1 M NaOH (25 mL) and ether-THF (1:1) (50 mL). The aqueous layer was separated and extracted with ether-THF (1:1) (25 mL). The combined organic extracts were dried ($Na_2SO_4$), filtered, and concentrated via rotary evaporation to give a dark-brown oil (432 mg). The oil was purified by column chromatography on silica gel, eluting with triethylamine-methanol (2.5:97.5). Selected fractions were combined and concentrated via rotary evaporation to give 180 mg (43.4%) of a dark-orange oil. $^1$H NMR ($CDCl_3$): δ 8.16 (d, 1H, J=1.8 Hz), 8.13(d, 1H, J=2.8 Hz), 7.14 (dd, 1H, J=1.9 Hz), 6.41 (d, 1H, J=16.0 Hz), 6.31–6.21 (dt, 1H, J=16.0, 6.9 Hz), 3.84 (s, 3H), 2.73 (t, 2H, J=6.8 Hz), 2.45 (s, 3H), 2.42 (dt, 2H, J=6.8, 1.1 Hz), 1.62 (br s, 1H). $^{13}$C NMR($CDCl_3$): δ 155.69, 140.64, 136.19, 133.63, 130.99, 127.94, 116.70, 55.51, 51.09, 36.35, 33.51.

For comparison purposes, Sample No. C-1 was provided. This sample is (S)-(–)-nicotine, which has been reported to have demonstrated a positive effect towards the treatment of various CNS disorders.

For comparison purposes, Sample No. C-2 is (E)-metanicotine which was provided generally using the techniques set forth by Laforge, *J.A.C.S.*, Vol. 50, p. 2477 (1928).

Determination of Binding of Compounds to Relevant Receptor Sites

Rats (Sprague-Dawley) were maintained on a 12 hour light/dark cycle and were allowed free access to water and food supplied by Wayne Lab Blox, Madison, Wis. Animals used in the present studies weighed 200 to 250 g. Brain membrane preparations were obtained from brain tissue of either males or females.

Rats were killed by decapitation following anesthesia with 70% $CO_2$. Brains were removed and placed on an ice-cold platform. The cerebellum was removed and the remaining tissue was placed in 10 volumes (weight:volume) of ice-cold buffer (Krebs-Ringers HEPES: NaCl, 118 mM; KCl, 4.8 mM; $CaCl_2$, 2.5 mM; $MgSO_4$, 1.2 mM; HEPES, 20 mM; pH to 7.5 with NaOH) and homogenized with a glass-Teflon tissue grinder. The resulting homogenate was centrifuged at 18,000×g for 20 min. and the resulting pellet was resuspeended in 20 volumes of water. After 60 min. incubation at 4° C., a new pellet was collected by centrifugation at 18,000×g for 20 min. After resuspension in 10 volumes of buffer, a new final pellet was again collected by centrifugation at 18,000×g for 20 min. Prior to each centrifugation step, the suspension was incubated at 37° C. for 5 min. to promote hydrolysis of endogenous acetylcholine. The final pellet was overlayered with buffer and stored at −70° C. On the day of the assay, that pellet was thawed, resuspended in buffer and centrifuged at 18.000×g for 20 min. The pellet obtained was resuspended in buffer to a final concentration of approximately 5 mg protein/ml. Protein was determined by the method of Lowry et al., *J. Biol. Chem.*, Vol. 193, pp. 265–275 (1951), using bovine serum albumin as the standard.

The binding of L-[$^3$H]nicotine was measured using a modification of the method of Romano et al., *Science*, Vol. 210, pp. 647–650 (1980) as described previously by Marks et al., *Mol. Pharmacol.*, Vol. 30, pp. 427–436 (1986). The L-[$^3$H]nicotine used in all experiments was purified chromatographically by the method of Romm, et al., *Life Sci.*, Vol. 46, pp. 935–943 (1990). The binding of L-[$^3$H]nicotine was measured using a 2 hr. incubation at 4° C. Incubations contained about 500 ug of protein and were conducted in 12 mm×75 mm polypropylene test tubes in a final incubation volume of 250 ul. The incubation buffer was Krebs-Ringers HEPES containing 200 mM TRIS buffer, pH 7.5. The binding reaction was terminated by filtration of the protein containing bound ligand onto glass fiber filters (Micro Filtration Systems) that had been soaked in buffer containing 0.5 percent polyethyleneimine. Filtration vacuum was −50 to −100 torr. Each filter was washed five times with 3 ml of ice-cold buffer. The filtration apparatus was cooled to 2° C. before use and was kept cold through the filtration process. Nonspecific binding was determined by inclusion of 10 uM nonradioactive nicotine in the incubations.

The inhibition of L-[$^3$H]nicotine binding by test compounds was determined by including one of eight different concentrations of the test compound in the incubation. Inhibition profiles were measured using 10 nM L-[$^3$H] nicotine and $IC_{50}$ values were estimated as the concentration of compound that inhibited 50 percent of specific L-[$^3$H] nicotine binding. Inhibition constants (Ki values), reported in nM, were calculated from the $IC_{50}$ values using the method of Cheng et al., *Biochem. Pharmacol.*, Vol. 22, pp. 3099–3108 (1973).

Determination of Dopamine Release

Dopamine release was measured by preparing synaptosomes from the striatal area of rat brain obtained from Sprague-Dawley rats generally according to the procedures set forth by Nagy et al., *J. Neurochem.*, Vol. 43, pp. 1114–1123 (1984). Striata from 4 rats were homogenized in 2 ml of 0.32M sucrose buffered with 5 mM HEPES (pH 7.5), using a glass-Teflon tissue grinder. The homogenate was diluted to 5 ml with additional homogenization solution and centrifuged at 1,000×g for 10 min. This procedure was repeated on the new pellet and the resulting supernatant was centrifuged at 12,000×g for 20 min. A 3 layer discontinuous Percoll gradient consisting of 16 percent, 10 percent and 7.5 percent Percoll in HEPES-buffered sucrose was made with the final pellet dispersed in the top layer. After centrifugation at 15,000×g for 20 min., the synaptosomes were recovered above the 16 percent layer with a Pasteur pipette, diluted with 8 ml of perfusion buffer (128 mM NaCl, 2.4 mM KCl, 3.2 mM $CaCl_2$, 1.2 mM $KH_2PO_4$, 1.2 mM $MgSO_4$, 25 mM HEPES pH 7.4, 10 mM dextrose, 1 mM ascorbate, 0.01 mM pargyline), and centrifuged at 15,000×g for 20 min. The new pellet was collected and re-suspended in perfusion buffer. The synaptosome suspension was incubated for 10 min. at 37° C. [$^3$H]-Dopamine (Amersham, 40–60 Ci/mmol) was added to the suspension to give a final concentration of 0.1 uM, and the suspension was incubated for another 5 min. Using this method, 30 to 90 percent of the dopamine was taken up into the synaptosomes, as determined by scintillation counting following filtration through glass fiber filters soaked with 0.5 percent polyethyleneimine. A continuous perfusion system was used to monitor release following exposure to each ligand. Synaptosomes were loaded onto glass fiber filters (Gelman type A/E). Perfusion buffer was dripped onto the filters (0.2–0.3 ml/min.) and pulled through the filters with a peristaltic pump. Synaptosomes were washed with perfusion buffer for a minimum of 20 min. before addition of the ligand. After the addition of 0.2 ml of a solution containing various concentrations of ligand, the perfusate was collected into scintillation vials at 1 min. intervals and the dopamine released was quantified by scintillation counting. Peaks of radioactivity released above background were summed and the average basal release during that time was subtracted from the total. Release was expressed as a percentage of release obtained with an equal concentration of (S)-(−)-nicotine.

Determination of Log P

Log P values (log octanol/water partition coefficient), which have been used to assess the relative abilities of compounds to pass across the blood-brain barrier (Hansch, et al., *J. Med. Chem.*, Vol. 11, p. 1 (1968)), were calculated according to the methods described by Hopfinger, *Conformational Properties of Macromolecules*, Academic Press (1973) using Cerius$^2$ software package by Molecular Simulations, Inc.

Determination of Interaction with Muscle

Human muscle activation was established on the human clonal line TE671/RD which is derived from an embryonal rhabdomyosarcoma (Stratton et al., *Carcinogen*, Vol. 10, pp. 899–905 (1989)). As evidenced through pharmacological (Lukas, *J. Pharmacol. Exp. Ther.*, Vol.251, pp. 175–182 (1989)), electrophysiological (Oswald et al, *Neurosci. Lett.*, Vol. 96, pp. 207–212 (1989)), and molecular biological studies (Luther et al., *J. Neurosci.*, Vol. 9, pp. 1082–1096 (1989)) these cells express muscle-like nicotinic receptors. Nicotinic acetylcholine receptor (nAChR) function was assayed using $^{86}$Rb$^+$ efflux according to a method described by Lukas et al., *Anal. Biochem.*, Vol. 175, pp. 212–218 (1988). Dose-response curves were plotted and the concentration resulting in half maximal activation of specific ion flux through nicotinic receptors determined for human muscle and rat ganglionic preparations (EC50). The maximal activation for individual compounds (Emax) was determined as a percentage of the maximal activation induced by (S)-(−)-nicotine.

Determination of Interaction with Ganglia

Ganglionic effects were established on the rat pheochromocytoma clonal line PC12, which is a continuous clonal cell line of neural crest origin derived from a tumor of the rat adrenal medulla expressing ganglionic-type neuronal nicotinic receptors (see Whiting et al., *Nature*, Vol. 327, pp. 515–518 (1987); Lukas, *J. Pharmacol. Exp. Ther.*, Vol. 251, pp. 175–182 (1989); Whiting et al., *Mol. Brain Res.*, Vol. 10, pp. 61–70 (1990)). Discussion concerning the heterogeneity of nicotinic receptors subtypes is set forth in Lukas et al., *Internatl. Review Neurobiol.*, Vol. 34, pp. 25–130 (1992). Acetylcholine nicotinic receptors expressed in rat ganglia share a very high degree of homology with their human counterparts. See, Fornasari et al., *Neurosci. Lett.*, Vol. 111, pp. 351–356 (1990) and Chini et al., *Proc. Natl. Acad. Sci. USA*, Vol. 89, pp. 1572–1576 (1992). Both clonal cell lines described above were maintained in proliferative growth phase according to routine protocols (Bencherif et al., *Mol. Cell. Neurosci.*, Vol. 2, pp. 52–65, (1991) and Bencherif et al.,*J. Pharmacol. Exp. Ther.*, Vol. 257, pp. 946–953 (1991)). Intact cells on dishes were used for functional studies. Routinely, sample aliquots were reserved for determination of protein concentration using the method of Bradford,*Anal. Biochem.*, Vol. 72, pp. 248–254 (1976) with bovine serum albumin as the standard.

Nicotinic acetylcholine receptor (nAChR) function was assayed using $^{86}$Rb$^+$ efflux according to a method described by Lukas et al., *Anal. Biochem.*, Vol. 175, pp. 212–218 (1988). Cells were plated in 35-mm diameter wells of 6-well dishes for at least 48 hours and loaded for at least 4 hours at 37° C. in a medium containing serum, and 1 $\mu$Ci/ml $^{86}$Rb$^+$. Following removal of the loading medium, cells were quickly washed three times with label-free Ringer's solution and exposed for 4 minutes at 20° C. to 900 $\mu$l of Ringer's containing the indicated concentration of compound to be tested (to define total efflux) or in addition to 100 $\mu$M mecamylamine (to define non-specific efflux). The medium was removed and $^{86}$Rb$^+$ was quantitated using Cerenkov detection (see Lukas et al., *Anal. Biochem.*, Vol. 175, pp. 212–218 (1988)). Specific ion efflux was determined as the difference in isotope efflux between total and non-specific efflux samples. Dose-response curves were plotted and the concentration resulting in half maximal activation of specific ion flux through nicotinic receptors determined for human muscle and rat ganglionic preparations (EC50). The maximal activation for individual compounds (Emax) was determined as a percentage of the maximal activation induced by (S)-(−)-nicotine.

Determination of Ion Flux from Thalamic Synaptosomes

Rat brains were dissected and midbrain (thalamus and mesencephalon) removed. The midbrain was then placed into a tube on ice, homogenized, and centrifuged at 2800 rpm for 10 minutes. The supernatant was collected and centrifuged for another 20 minutes at 9650 rpm. The resulting pellet was resuspended by trituration in 700 ul ice cold perfusion buffer. Synaptosomes were then loaded with $^{86}$Rb+ Ion efflux was determined using the methods of Marks et al., *J. Pharmacol. Exp. Ther.*, Vol. 264, pp. 427–436 (1993). Total efflux was determined by subtraction of basal release from release at stimulation (total peak release). The ratio of the peak to baseline (Rp) was calcu lated for each concentration. A tetramethylammonium control (i.e., a full agonist to the receptor of interest) is used in each assay to compare each agonist's ability to stimulate rubidium efflux to the control. Emax values are reported as a percent of Emax for tetramethylammonium.

TABLE I

| | Sample No. | | | | |
|---|---|---|---|---|---|
| | 1 | 2 | 3 | C-1* | C-2* |
| Ki (nm) | 9 | 82 | 7 | 4 | 26 |
| log P | 2.37 | 2.24 | 1.84 | 0.71 | 1.39 |
| Receptor Activation | | | | | |
| Emax (%) | 67 | 35 | 62 | 87 | 79 |
| EC50 (nm) | 269 | 1,700 | 470 | 591 | 732 |
| Dopamine Release | | | | | |
| Emax (%) | 124 | 182 | 106 | 100 | 81 |
| EC50 (nm) | 287 | 21,400 | 2,341 | 100 | 1,158 |
| Muscle Effect | | | | | |
| Emax (%) | 0 | 4 | 0 | 100 | 0 |
| EC50 | NM | NM | NM | 80,000 | NM |
| Ganglion Effect | | | | | |
| Emax (%) | 0 | 6 | 0 | 100 | 0 |
| EC50 | NM | NM | NM | 20,000 | NM |

*not an example of the invention
NM not meaningful, due to lack of effect

The data in Table I indicate that the compounds have the capability of passing the blood-brain barrier by virtue of their favorable log P values, binding to high affinity CNS nicotinic receptors as indicated by their low binding constants, and activating CNS nicotinic receptors of a subject and causing neurotransmitter release, thereby demonstrating known nicotinic pharmacology. Thus, the data indicate that such compounds have the capability of being useful in treating CNS disorders involving nicotinic cholinergic systems. Furthermore, the data indicate that the compounds do not cause any appreciable effects at muscle sites and ganglionic sites, thus indicating a lack of undesirable side effects in subjects receiving administration of those compounds.

What is claimed is:
1. A compound having the formula:

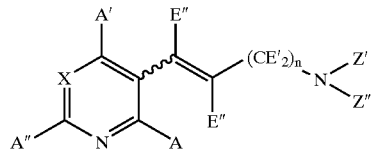

wherein X is selected from the group consisting of C—H, C—F, C—Cl, C—Br, C—I, C—NR'R", C—CF$_3$, C—CN, C—C$_2$R', C—SCH$_3$, C—N$_3$, C—SO$_2$CH$_3$, C—OR', C—SR', C—C(=O)NR'R", C—NR'C(=O)R', C—(C=O)R', C—C(=O)OR', C—CH$_2$R', C—OC(=O)R', C—OC(=O)NR'R" and C—NR'C(=O)OR' where R' and R" are individually hydrogen or C$_{1-5}$ alkyl, n is 2, 3, 4, 5, 6, or 7, Z' and Z" individually represent hydrogen or C$_{1-5}$ alkyl, at least one of Z' or Z" is C$_{1-5}$ alkyl;

A, A' and A" individually represent hydrogen or C$_{1-5}$ alkyl or halo C$_{1-5}$ alkyl;

E' and E" individually represent H, C$_{1-5}$ alkyl or halo C$_{1-5}$ alkyl; and at least one E' at the alpha position to the NZ'Z" group represents C$_{1-5}$ alkyl.

2. The compound of claim 1, wherein one of Z' and Z" is methyl and the other is hydrogen.
3. The compound of claim 1, wherein Z' and Z" are both methyl.
4. The compound of claim 1, wherein Z" is methyl.
5. The compound of claim 1, wherein X is C—OR'.
6. The compound of claim 5, wherein R' is ethyl, methyl or isopropyl.
7. The compound of claim 1, wherein n is 2.
8. The compound of claim 1, wherein A, A' and A" are hydrogen.
9. The compound of claim 1, wherein the wavy line in the structure represents the trans (E) form.
10. The compound of claim 4, wherein the wavy line in the structure represents the trans (E) form.
11. The compound of claim 5, wherein the wavy line in the structure represents the trans (E) form.
12. The compound of claim 1, wherein A is hydrogen.

* * * * *